US007199280B2

(12) United States Patent
Te Riele et al.

(10) Patent No.: US 7,199,280 B2
(45) Date of Patent: Apr. 3, 2007

(54) HOMOLOGOUS RECOMBINATION IN MISMATCH REPAIR INACTIVATED EUKARYOTIC CELLS

(75) Inventors: Henricus Petrus Joseph Te Riele, Amsterdam (NL); Niels De Wind, Leiderdorp (NL); Helena Maria Johanna Dekker-Vlaar, Obdam (NL)

(73) Assignee: Mixis France S.A., Paris (FR)

( * ) Notice: Subject to any disclaimer, the term of this patent is extended or adjusted under 35 U.S.C. 154(b) by 0 days.

(21) Appl. No.: 09/884,877

(22) Filed: Jun. 20, 2001

(65) Prior Publication Data

US 2002/0151059 A1    Oct. 17, 2002

Related U.S. Application Data

(63) Continuation-in-part of application No. 09/147,712, filed as application No. PCT/EP95/02980 on Jul. 26, 1995, now abandoned.

(51) Int. Cl.
*C12N 5/00* (2006.01)
*C12N 15/00* (2006.01)
*A01K 67/00* (2006.01)
*A01K 67/027* (2006.01)

(52) U.S. Cl. ............................ 800/21; 800/18; 800/25; 435/325

(58) Field of Classification Search ................ 424/9.1, 424/9; 435/354; 800/2
See application file for complete search history.

(56) References Cited

U.S. PATENT DOCUMENTS 5,789,215 A * 8/1998 Berns et al. ............. 435/172.3

FOREIGN PATENT DOCUMENTS

WO        90/07576      7/1990
WO        93/01292      1/1993

OTHER PUBLICATIONS

WO 93/04169 "Gene targeting in animal . . ." Berns et al., Mar. 4, 1993.*
Varlet et al. "Cloning and expression . . ." NAR 22(25):5723-5728, 1994.*
Orth et al. "Genetic instability in human . . ." PNAS 91:9495-9499, Sep. 1994.*
Umar et al. "Defective mismatch repair . . . " JBC 269(20): 14367-14370, May 20, 1994.*
Reenan et al. "Characterization of insertion . . . " Genetics 132:975-985, Dec. 1992.*
X81143, locus MMSH2GEN, *M. musculus* msh2 Feb. 16, 1995.*
Promega Protocols and Appliccation Guide, Second Edition, Promega Corp, p. 28, Mar. 1991.*
Selve, E. et al., "Mismatch Correction Acts As A Barrier To Homologous Recombination in *Saccharomyces cerevisiae*", *Genetics*, vol. 139:1175-1118, (1995).
Rayssiguier, C. et al., "The Barrier To Recombination Between *Escherichia coli* and *Salmonella typhimurium* Is Disrupted In Mismatch-Repair Mutants", *Nature*, vol. 342:396-400, (1989).
Te Riele, H. et al., "Highly Efficient Gene Targeting In Embryonic Stem Cells Through Homologous Recombination With Isogenic DNA Constructs", *Proceedings Of The National Academy Of Sciences of USA*, vol. 89:5128-5132, (1992).
Varlet, I. et al., "Cloning And Expression Of the Xenopus and Mouse Msh2 DNA Mismatch Repair Genes", *Nucleic Acids Research*, vol. 22(25):5723-5728, (1994).

* cited by examiner

*Primary Examiner*—Joseph Woitach
(74) *Attorney, Agent, or Firm*—Foley & Lardner LLP

(57) ABSTRACT

A mammalian cell having a mismatch repair-deficient phenotype is provided, where one or both alleles of a gene essential for mismatch repair, such as an Msh gene, are inactivated. Using this cell in a gene knock-out methodology advantageously allows efficient homologous recombination, even when the DNA sequences of the donor and recipient sequences diverge by significantly more than 0.6%.

14 Claims, 2 Drawing Sheets

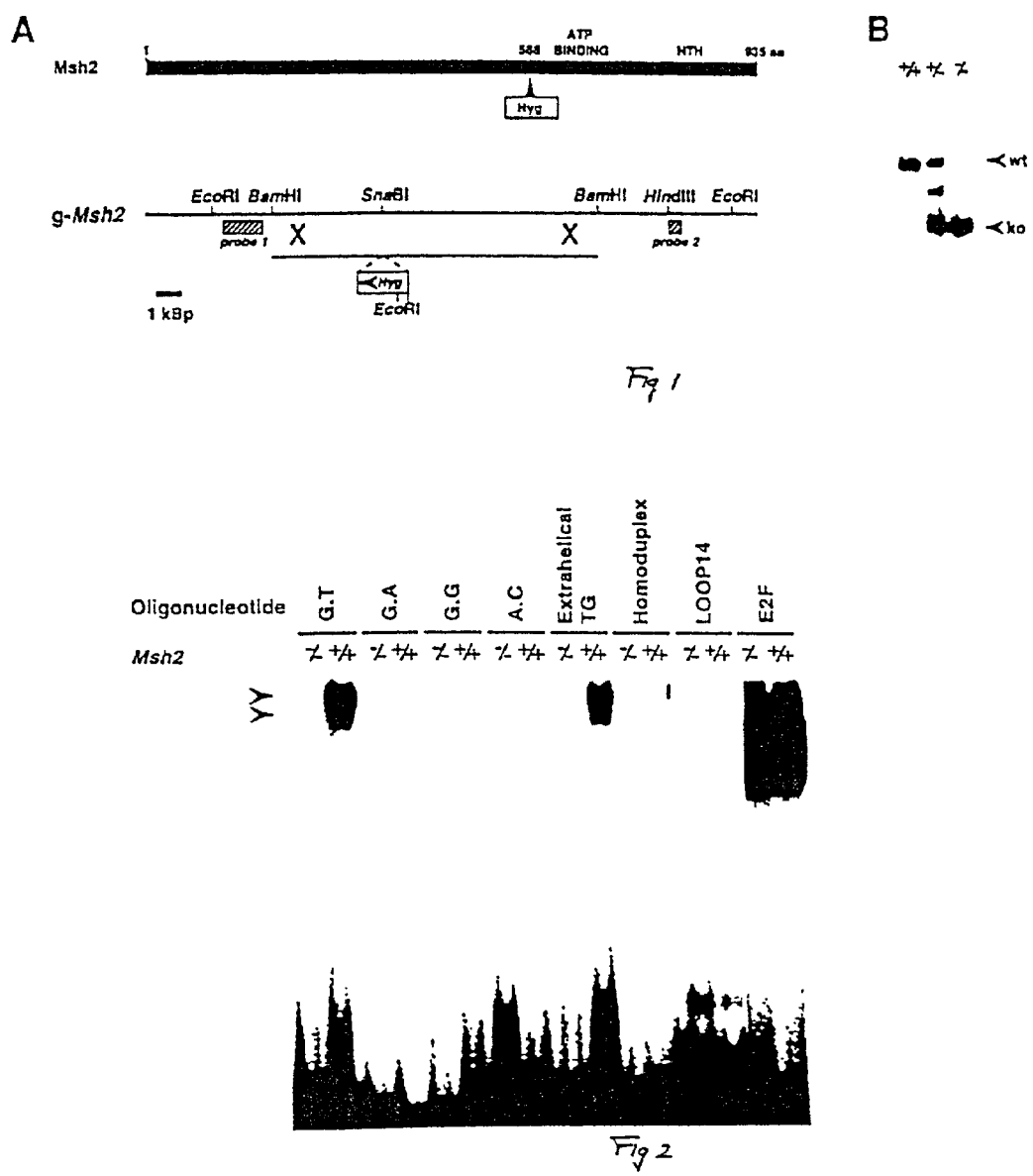
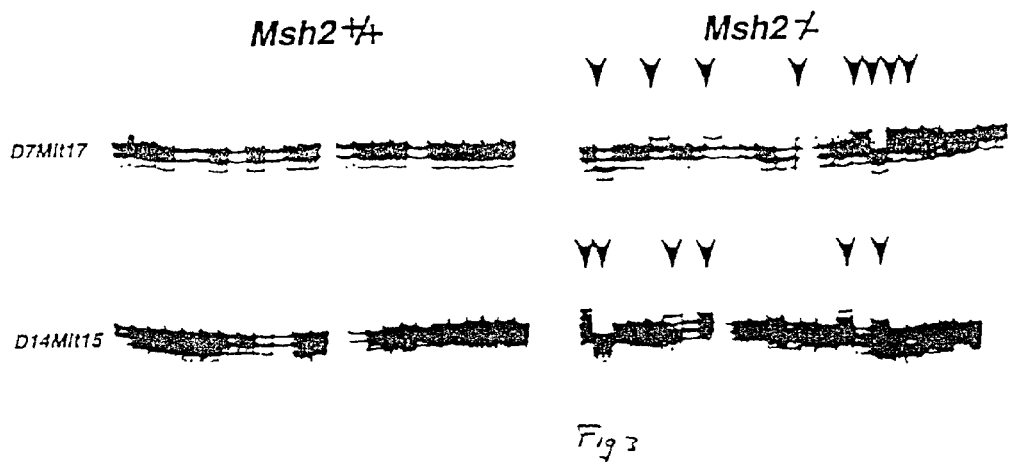

SEQUENCE LISTING

<160> NUMBER OF SEQ ID NOS: 8

<210> SEQ ID NO 1
<211> LENGTH: 38
<212> TYPE: DNA
<213> ORGANISM: Mus sp.

<400> SEQUENCE: 1
gggaagctgc caggcccag tgtcagcctc ctatgctc                    38

```
<210> SEQ ID NO 2
<211> LENGTH: 38
<212> TYPE: DNA
<213> ORGANISM: Mus sp.

<400> SEQUENCE: 2
gagcatagga ggctgacatt ggggcctggc agcttccc                        38

<210> SEQ ID NO 3
<211> LENGTH: 38
<212> TYPE: DNA
<213> ORGANISM: Mus sp.

<400> SEQUENCE: 3
gagcatagga ggctgacaat ggggcctggc agcttccc                        38

<210> SEQ ID NO 4
<211> LENGTH: 38
<212> TYPE: DNA
<213> ORGANISM: Mus sp.

<400> SEQUENCE: 4
gagcatagga ggctgacagt ggggcctggc agcttccc                        38

<210> SEQ ID NO 5
<211> LENGTH: 38
<212> TYPE: DNA
<213> ORGANISM: Mus sp.

<400> SEQUENCE: 5
gagcatagga ggctgacacc ggggcctggc agcttccc                        38

<210> SEQ ID NO 6
<211> LENGTH: 39
<212> TYPE: DNA
<213> ORGANISM: Mus sp.

<400> SEQUENCE: 6
gagcatagga ggctgacact ggggcctgg cagcttccc                        39

<210> SEQ ID NO 7
<211> LENGTH: 38
<212> TYPE: DNA
<213> ORGANISM: Mus sp.

<400> SEQUENCE: 7
gagcatagga ggctgacact ggggcctggc agcttccc                        38

<210> SEQ ID NO 8
<211> LENGTH: 52
<212> TYPE: DNA
<213> ORGANISM: Mus sp.

<400> SEQUENCE: 8
gagcatagga ggctgacaca tacgtgagta ctctggggcc tggcagcttc cc        52
```

HOMOLOGOUS RECOMBINATION IN MISMATCH REPAIR INACTIVATED EUKARYOTIC CELLS

RELATED APPLICATIONS

This application is a continuation-in-part of U.S. application Ser. No. 09/147,712, filed Feb. 23, 1999 now abandoned, which was the National Stage of International Application No. PCT/EP95/02980, filed Jul. 26, 1995 and published in the English language. The entire content of these prior applications is herein incorporated by reference.

BACKGROUND OF THE INVENTION

The introduction of specific modifications in the prokaryotic and eukaryotic genome is a powerful tool in studying gene function both at the level of individual cells and in the context of a complete organism. In addition, modification of specific genes may result in the generation of industrially and medically important organisms, whereas correction of defective alleles in eukaryotic cells may provide a substantial step forward in the development of somatic gene-therapy protocols.

The method of genetic modification relies on the ability of virtually every cell type to exchange DNA sequences with a high degree of nucleotide sequence similarity by a process which is called homologous recombination (Kucherlapati R. et al., 1988). Briefly, the method of genetic modification involves the generation of a so-called targeting construct, a DNA sequence that is largely identical to the specific chromosomal locus to be modified, but differing from this locus by specific modifications. These modifications can be as small as the deletion, insertion or substitution of a single base-pair, or be as large as the deletion or insertion of ten's of kilobase pairs. On entry of the targeting construct into the cell, exchange of sequences flanking the modification with their chromosomal counterparts, will result in the introduction of the modification into the recipient chromosome.

The efficiency of homologous recombination in both prokaryotes and eukaryotes strongly depends on complete sequence identity of exchanging DNA strands (Schen, P. et al., 1986; Nassif, N., et al. 1993; Waldman, A. S. et al., 1988; Te Riele, H., 1992). Thus, sequence dissimilarities as small as 0.5% can already strongly impede homologous recombination. In several bacterial species, *Escherichia coli, Salmonella typhimurium* and *Streptococcus pneumoniae* as well as in the yeast *Saccharomyces cerevisiae* it has been unequivocally shown that the DNA mismatch repair system is responsible for suppressing recombination between homologous but non-identical DNA sequences (Rayssiguier, C. et al., 1989; Claverys, J. P. et al., 1986; Selva, E. et al., 1995).

Genetic Modification of Mice

The introduction of specific genetic alterations into the germ line of mice was made possible by a combination of new techniques in molecular biology and embryology that have become available during the last ten years (Capecchi, M. et al. 1989; Frohman, M. A. et al., 1989; Hogan, B. 1994). The method entails the introduction of a planned genetic modification in embryonic stem (ES) cells by homologous recombination. ES cells are originally derived from the inner cell mass of 3.5 day old pre-implantation embryos and can be maintained by in vitro culture as immortalized cell lines, retaining the undifferentiated state under appropriate culture conditions. At present, a number of ES cell lines are available. ES cells injected into the blastocoel of 3.5 day blastocyst-stage embryos can efficiently compete with the inner-cell-mass cells of the recipient blastocyst in embryonic development thus generating a chimeric mouse consisting of cells derived from the recipient blastocyst and the injected ES cells. Should the in vitro modified ES cells contribute to the germ line of chimeric animals, the ES cell genome can be transmitted to the next generation resulting with animals that carry the introduced modification in all their cells. Intercrossing of such animals reveals the phenotypic consequences of homozygosity of the modified gene.

The most commonly introduced genetic modification in ES cells is gene disruption leading to gene inactivation. This allows the study of gene function by analyzing the consequences of the absence of a particular gene in the context of a complete organism. Also, many hereditary human diseases result from homozygosity, i.e. presence of two defective alleles, of specific genes [e.g., cancer predisposition syndromes like hereditary nonpolyposis colorectal cancer (Modrich, P., 1994), Li Fraumeni syndrome (Malkin et al., 1990), retinoblastoma (Hansen, M. F., 1988)]. The generation of mouse models for such diseases by disruption of the mouse homologues of the genes involved provides an invaluable tool for studying hereditary diseases in an experimental setting.

Gene Disruption in ES Cells

The inactivation of a specific gene in ES cells via homologous recombination starts with the preparation of a DNA targeting construct (Thomas, K. R. et al., 1987). Two types of targeting constructs can be used. In a replacement-type vector, a drug-resistance marker gene (conferring to the cell resistance to drugs like G418, Hygromycin B, Puromycin, Histidinol) disrupts a sequence which is homologous to a sequence in or around the target gene in the recipient genome; in an insertion-type vector the marker gene flanks the homologous sequence. The targeting construct is introduced into ES cells by electroporation (or alternatively by Ca-Phosphate precipitation, liposome-mediated DNA transfer or micro-injection) and cells are selected for stable integration of the targeting construct into the recipient genome by growth in medium containing the appropriate drug. Drug-resistant colonies are the result of either one of two events: integration of the targeting construct at a random site in the genome or integration of the marker gene in the target locus via homologous recombination between the flanking sequences and their chromosomal counterparts. The replacement-type vector integrates by homologous recombination on both sides of the marker gene: the insertion-type vector integrates by a single homologous recombination event leading to duplication of the region of homology. Thus, the marker gene serves two purposes: it allows selection of cells that have taken up the targeting construct and, on integration via homologous recombination, it will disrupt the target gene thereby modifying its function.

Distinguishing ES cell clones resulting from homologous recombination from those resulting from random integration, requires the DNA of individual clones to be analyzed by Southern hybridization or the polymerase chain reaction.

Unfortunately, in many targeting experiments, random integration was often found to be far more efficient than homologous recombination and also large variations in targeting efficiency were observed for different genes (Camerini-Otero, R. D. et al. 1990). In this respect, mammalian cells differ from bacteria and lower eukaryotes like yeast (Sulston, J. E. et al., 1977), *Leishmania major* (Cruz., A., 1990) or *Trypanosoma brucei* (Ten Asbroek, A. et al., 1990), where integration of exogenous DNA into the recipient genome exclusively or predominantly occurs via homologous recombination. To date, three factors clearly affecting the recovery of homologous recombinants in mammalian cells have been identified. First, the frequency of homologous recombination increases substantially with the total length of the homologous sequences up to 14 kilobase pairs (Deng, C. et al., 1992). Second, the expression level of the marker gene at the target locus affects the frequency of recovery of homologous recombinants: low expression may lead to loss of homologous recombinants, whereas high expression may allow selection of homologous recombinants at an elevated drug concentration (Hanson, K. D. et al., 1993). Third, sequence dissimilarities between the targeting construct and the chromosomal target locus strongly suppress the efficiency of homologous recombination (Te Riele, H. et al., 1992).

High Efficiency Targeting with Isogenic DNA Constructs

The suppression of homologous recombination in ES cells by small sequence dissimilarities became clear by a gene targeting experiment aimed at disrupting the Retinoblastoma gene with a neomycin resistance marker gene. Two targeting constructs were prepared carrying the neomycin resistance marker embedded in 10.5 kb of Rb sequence. In one construct the Rb sequence was derived from an isogenic mouse strain 129, and was therefore identical to the corresponding chromosomal locus in the ES cells, which were also derived from mouse strain 129. In the other construct, the Rb sequence was derived from a non-isogenic mouse strain BALB/c (Te Riele et al., 1992; Table 1). The two constructs contained corresponding Rb sequences and were therefore largely similar. However, they differed approximately 0.6% at the nucleotide level (which corresponds to the level of sequence polymorphism found in the human population). Thus, in a stretch of 1687 base pairs that was sequenced, the BALB/c sequence differed from the 129 sequence by 9 base pair substitutions, three small deletions (of 1, 4 and 6 nucleotides) and two polymorphic CA-repeats (see Te Riele et al., 1992). On introduction of these constructs in 129-derived ES cells, homologous recombination at Rb with the 129-derived construct was 50-fold more efficient than with the nonisogenic BALB/c-derived construct. To provide additional evidence that the suppression of recombination was solely dependent on the polymorphisms between the endogenous locus and the targeting DNA, the inverse experiment was performed, i.e. targeting of a BALB/c-derived ES cell line with the 129- and BALB/c-derived constructs. This experiment yielded the inverse result, i.e. a higher targeting efficiency with the BALB/c-derived construct than with the nonisogenic 129-derived construct.

With a somewhat different targeting construct, consisting of a hygromycin resistance gene embedded in 17 kb of isogenic Rb DNA, we observed that 80% of all Hygromycin B-resistant colonies resulted from homologous recombination (Te Riele et al., 1992). This demonstrates that, in the presence of perfect homology, also in mammalian cells homologous recombination rather than random integration can be the predominant event.

Although clearly not all problems of gene targeting have been solved, many genes have now been successfully targeted by the use of isogenic DNA targeting constructs. However, genetic modification of cells derived from an outbred organism can become a difficult endeavor as isogenic targeting constructs are not easily available. In this case, efficient gene targeting would require the targeting construct to be prepared from DNA derived from the target cell. Especially in the context of gene therapy, this would raise a tremendous practical obstacle to correction of a defective gene. Also, base sequence divergence imposes a major barrier to exchanging a large chromosomal region of one species by the syntenic region of another species.

The Introduction of Subtle Mutations

A related problem exists in methodologies to introduce subtle mutations into the germ line of a transgenic animal. Although protocols for disruption of genes in inbred ES cell lines (and in somatic cell lines of which isogenic DNA targeting constructs can be prepared) are rather well developed, the introduction of more subtle mutations is not straightforward. Current protocols are variations on a two-step procedure in which first a marker gene is introduced into the target gene followed by replacement of the marker gene by the desired subtle mutation (Te Riele, H. et al., 1992). This procedure requires the marker gene to be selectable both for its presence (first step) and its absence (replacement by the subtle mutation).

Useful marker genes are the Hprt minigene to be used in Hprt-deficient ES cells (positive selection in HAT medium: negative selection by 6-thioguanine) and a combination of the neomycin resistance gene (positive selection by G418) and the Herpes Simplex Virus thymidine kinase gene (negative selection by Gancyclovir). In an alternative procedure, the subtle mutation and the marker gene are present on the same targeting construct and concomitantly introduced into the genome by homologous recombination. If an insertion-type vector was used, the marker gene can be removed by intrachromosomal recombination between the duplicated sequences that were generated during the first integration event (Hasty, P. et al., 1993). In case of a replacement-type vector, the marker gene can be removed if it was flanked by two site-specific-recombination sites (e.g. loxP sites). Recombination between these sites on introduction into the cell of the loxP-specific recombinase Cre will remove the marker gene from the genome (Kilby, N. et al., 1993).

Although either of the above mentioned procedures has allowed the subtle modification of a number of genes in ES cells, they are highly demanding as to the generation of appropriate DNA targeting constructs and the culturing of ES cells under various selective conditions.

Therefore, an attractive alternative to these procedures might be the use of small single- or double-stranded oligonucleotides (up to 100 bases or base pairs), which are identical to the target locus except for one or several base pair alterations. However, our finding that base sequence dissimilarities as small as 0.6% strongly suppress homologous recombination, may impose a major impediment to using such oligonucleotides for the introduction of subtle genetic modifications. There is thus a need in the art to allow the subtle modification of cell lines and cells derived from living organisms and temporarily cultured in vitro.

SUMMARY OF THE INVENTION

The present invention provides a method to genetically modify a eukaryotic cell's mismatch repair system in order to allow homologous genetic recombination to occur with non-identical genetic sequences. The present methodology thus overcomes the major barrier that sequence divergence has imposed on prior homologous genetic recombination methodologies. The present invention also can be used to create genetically modified embryonic stem cells which can be used to generate chimeric animals and chimeric plants that can transmit the mutated genome through the germ line. A cell line derived from any mammalian species or mammalian organ, from any organism containing non-identical homologous chromosomes, or from any plant species and cultured in vitro can be used for the target cell. This modified target cell can be reintroduced into the organism. The present invention further provides a method to derive cells or cell lines from mismatch repair deficient mice carrying a disruption in both copies of the Msh2 gene or another mismatch repair gene.

The invention also provides the introduction of subtle modification of cell lines and cells derived from living organisms and temporarily cultured in vitro. Such subtle mutations may be introduced by targeting DNA that can be derived from the same species as the target cell and modified in vitro at specific sites to deliberately introduce sequence divergence. Alternatively, the targeting DNA can be derived from the same species as the target cell, where the DNA is non-isogenic with the target cell DNA, and where the two sequences differ up to 5% at the nucleotide level. In another embodiment, the targeting DNA can be derived from another species as the target cell, and targeting sequence and the target locus can differ by up to 30% sequence divergence in the region where homologous recombination can take place, wherein the targeting DNA may be a chromosomal DNA fragment carried on a YAC or cosmid vector. In yet another embodiment, the targeting DNA is a double- or single-stranded oligonucleotide consisting of 10–100 bases or base pairs of which one or several bases or base pairs differ from the target locus.

The targeting DNA may be constructed in such a way to allow the generation of deletions of chromosomal regions. A targeting construct thus may consist of any selectable marker gene flanked by two sequences that can combine with chromosomal loci: one flanking sequence being identical or highly homologous (>95% sequence identity) to a sequence of the genome of the target cell, the other flanking sequence being a so-called repetitive sequence. A repetitive sequence may be selected from a sequence having numerous diverged copies spread over the genome, such as a long interspersed element (LINE), a short interspersed element (SINE), e.g. an Alu sequence, or a transposon or retroviral sequence. Alternatively, a targeting construct may consist of any selectable marker gene flanked by two sequences, one being a sequence that acts as a telomere, the other flanking sequence being a repetitive sequence having numerous diverged copies are spread over the genome.

BRIEF DESCRIPTION OF THE DRAWINGS

FIG. 1. Targeted disruption of the mouse Msh2 gene.

Figure 4:
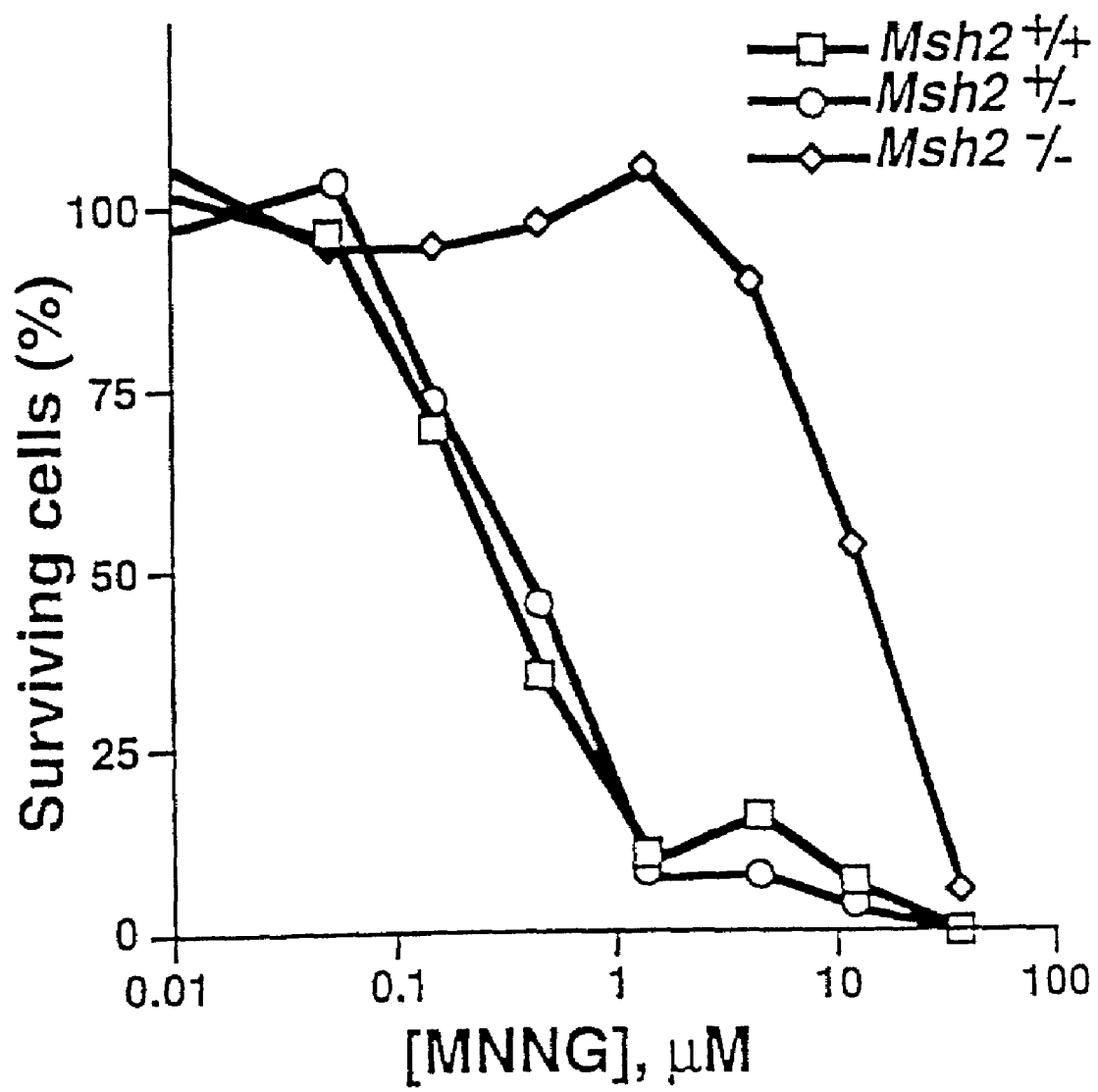

A: Top: schematic diagram of the mouse Msh2 protein. ATP binding and HTH: putative ATPase and helix turn helix domains, respectively (Valet et al., 1994). The position at which the protein is disrupted by insertion of the Hyg maker is indicated. Bottom: the genomic Msh2 locus; indicated below is the targeting construct carrying the Hyg maker inserted into a unique SnaB I site within an exon sequence of Msh2. The positions of the external probes used for detection of targeting events are indicated.

B: The Msh2 locus in Msh2+/+ cell line wt-2, Msh2+/− cell line sMsh2-55 and Msh2−/− cell line dMsh2-9. Genomic DNA of these cell lines was digested with EcoRI and analyzed by Southern hybridization using probe 1 (FIG. 1A). Arrowheads indicate the positions of the wild type (wt, 20 kbp), and disrupted (ko, 7.5 kbp) alleles.

FIG. 2. Mismatch-binding activity in wild-type and Msh2-deficient cells.

Binding activity in extracts of Msh2+/+ cell line wt-2 and Msh2−/− cell line dmsh2-9 to double-stranded oligonucleotides containing a mismatch (G.T, G.A, G.G, or A.C), an extrahelical dinucleotide (Extrahelical TG), or an extrahelical 14-nucleotide loop (LOOP 14) and a Homoduplex was assessed using a gel retardation assay. Sequences of the oligonucleotides are given under Experimental Procedures. Arrowheads indicate the positions of mismatch-specific complexes. E2F: Binding to an oligonucleotide carrying an E2F site served as a positive control (Beijersbergen et al., 1995).

FIG. 3. Microsatellite stability in wild-type and Msh2-deficient cells.

Genomic DNA of 24 subclones derived from Msh2+/+ cell line wt-2 and Msh2−/− cell line dmsh2-9 was amplified by PCR using primer sets D7Mit17 and D14Mit15. Arrowheads indicate microsatellite alleles with a detectable length alteration.

FIG. 4. Tolerance of Msh2-deficient cells to the simple methylating agent MNNG.

ES cell lines wt-2 (Msh2+/+), sMsh2-55 (Msh2+/−) and dMsh2-9 (Msh2−/−) were exposed to increasing amounts of MNNG for one hour in the presence of $O^6$-benzylguanine. After four days of incubation, cells were trypsinized and counted.

DETAILED DESCRIPTION OF THE PREFERRED EMBODIMENTS

We now have demonstrated that in mammalian cells deficient for the DNA mismatch repair gene Msh2, homologous recombination has lost the requirement for complete sequence identity between exchanging DNA sequences. This finding provides a new method for modifying the eukaryotic genome using DNA targeting constructs which substantially differ from the target locus in the region where recombination takes place by genetically and/or functionally inactivating the cell's mismatch correction system.

Because inactivation of the DNA mismatch repair system eliminates the requirement for DNA targeting constructs that are largely identical to the target locus, efficient genetic modification of both somatic cells and the germ line of outbred organisms is possible. The present technique thus provides a means for somatic gene therapy and the modification of eukaryotic species of which inbred strains are not easily available. Additionally, genomic sequences can be replaced by small oligonucleotides carrying one or more base pair alterations or by large chromosomal sequences derived from other species. Large deletions by intra- or extrachromosomal homologous recombination between repeated but diverged sequences can be created from the use of this method.

The DNA mismatch repair system can be inactivated (1) by disrupting both copies of one of the genes essential to the mismatch repair system, (2) by introducing antisense RNA constructs, driven by an appropriate promoter, thus functionally inactivating one of the genes essential for DNA mismatch repair, (3) by introducing a modified antisense oligodeoxynucleotide, thus functionally inactivating one of the genes essential for DNA mismatch repair, (4) by expression of a dominant negatively acting version of a gene involved in DNA mismatch repair, or (5) by saturation of the mismatch repair system through the introduction into the cell of DNA molecules carrying one or more mis- or unpaired bases.

A gene targeting assay may be used to test whether the cellular mismatch repair system has been inactivated. This test compares the targeting efficiency of isogenic versus nonisogenic DNA targeting constructs or assesses intrachromosomal recombination between homologous, but diverged, DNA sequences. Further, homologous recombination can be tested by using an Embryonic Stem cell line or any other cell line in which the mismatch repair system is inactivated by disruption of one or both copies of the Msh2 gene or another mismatch repair gene.

The targeting DNA may be constructed in such a way to allow the generation of deletions of chromosomal regions. A targeting construct thus may consist of any selectable marker gene flanked by two sequences that can combine with chromosomal loci: (1) one flanking sequence being identical or highly homologous (>95% sequence identity) to a sequence of the genome of the target cell, the other flanking sequence being a so-called repetitive sequence, or (2) one being a sequence that acts as a telomere, the other flanking sequence being a repetitive sequence. A repetitive sequence may be selected from a sequence having numerous diverged copies spread over the genome, such as a long interspersed element (LINE), a short interspersed element (SINE), e.g. an Alu sequence, or a transposon or retroviral sequence. Repetitive sequences are described in Watson et al., 1995, for example.

As described above, base sequence dissimilarities as modest as 0.6% impose a strong barrier to efficient homologous recombination in mouse embryonic stem cells (Te Riele et al., 1992). Suppression of homologous recombination by small base sequence divergences was earlier observed in bacteria (*E. coli*, *S. typhimurium* and *S. pneumoniae*), yeast and mouse fibroblasts (Schen, P., 1986; Nassif, N., 1993; Waldman, A. S., 1988). The role of the DNA mismatch correction system in suppressing recombination between homologous but diverged sequences, was most dramatically demonstrated by Radman and coworkers in studying bacterial conjugation between the related but diverged species *Escherichia coli* and *Salmonella typhimurium* (Rayssiguier, C., 1989). This process relies on entry of chromosomal fragments of one species into the other and recombination of these fragments with the chromosome of the recipient bacterium. The sequence divergence between the two species is estimated to be 20–30% and therefore the recovery of exconjugants from an interspecies cross is about $2 \times 10^5$-fold lower than from an intraspecies cross. However, the recovery of exconjugants from the interspecies cross increased $3 \times 10^3$-fold if the recipient bacteria carried an inactivating mutation in either the mutS or mutL gene, both of which being essential for DNA mismatch correction.

The central protein in DNA mismatch correction in *E. coli* is encoded by the mutS gene (Modrich, P., 1991). It recognizes and binds to base mispairs and small loops of up to four unpaired nucleotides. After binding to heteroduplex DNA, the MutS-DNA complex is bound by the mutL gene product which leads to excision of a tract of single-stranded DNA of up to several kilobases that contains the mispaired nucleotide(s). In this process also the mutU gene product plays a role, whereas the mutH gene product ensures removal of newly synthesized strands rather than parental strands. The repair process is completed by re-synthesis of the excised strand and ligation of the remaining nick. Mismatch repair in *E. coli* is responsible for maintaining genome stability in at least two ways:

i) by recognizing and repairing mis- and unpaired nucleotides that occur, respectively, by misincorporation and slippage during DNA replication;

ii) by recognizing mismatches occurring in heteroduplexes formed at initial stages of recombination between homologous but not-identical sequences.

This may either lead to blocking elongation of heteroduplex formation or dissociation of the heteroduplex thus aborting the recombination reaction. Consequently, *E. coli* strains defective for either mutS or mutL have a pleiotropic phenotype: an increased mutation rate, including destabilization of simple-sequence repeats and an increased rate of recombination between homologous but diverged DNA sequences. The latter phenotype is clearly manifested by the efficient recovery of recombinant bacteria resulting from conjugational crosses between the related but diverged species *Escherichia coli* and *Salmonella typhimurium* wherein the recipient bacterium was deficient for mutS or mutL (Rayssiguier, C. et al., 1989). Also, the frequency of chromosomal rearrangements by ectopic recombination between diverged sequences is substantially elevated in mismatch repair deficient bacteria (Petit, M. A. et al., 1991).

In many respects, the biochemistry of mismatch repair systems in eukaryotes resembles that of the *E. coli* mutS,L system. Homologs of both genes have been identified in yeast and mammalian cells. Based on mismatch binding in vitro, and on the mutator and recombinator phenotypes of *Saccharomyces cerevisiae* mutants, the protein encoded by the yeast MSH2 gene seems to be the functional homologue of MutS (Reenan, R. A. G. et al., 1992; Miret, J. J. et al., 1993; Alani, E. et al., 1995). A homolog of the yeast MSH2 gene was identified in mammalian cells by analysis of a G·T-mismatch-binding activity, positional cloning and PCR amplification of mouse DNA using degenerate primers (Varlet, I. et al., 1994). Similarly, homologues of the *E. coli* mutL gene were identified in yeast and mammalian cells.

Interestingly, inherited mutations in human muts and mutL homologues were recently found to be related to the cancer predisposition syndrome HNPCC (hereditary non-polyposis colorectal cancer), which is characterized by development of tumors of the proximal colon at early age. In these tumors, mismatch repair is lost, as manifested by destabilization of simple sequence repeats, the replication error-positive (RER+) phenotype (Modrich, P., 1994).

Experimental Methods Used and Results

We demonstrate:
- a method of the inactivation of the mismatch repair system by knocking out the function of msh2 gene;
- the consequences of the mismatch repair inhibition on the phenotype of the embryonic stem cells;
- the effect of inhibiting the mismatch repair system on recombination of diverged sequences; and
- the effect of knockout of the msh2 genes on phenotype of a transgenic mouse.

Knockout of msh2 Gene in Embryonic Stem Cells

To demonstrate the role of the mammalian Msh2 gene in DNA mismatch repair and to address the role of mismatch repair in maintaining genome stability, we generated an ES cell line carrying a disruption in both copies of the mouse Msh2 gene. This line is designated dMsh2-9.

Disruption of Msh2 in Mouse ES Cells

Genomic Msh2 fragments were obtained by screening a 1290LA-derived genomic DNA library with a murine Msh2 cDNA probe (Varlet et al., 1994). The targeting construct was prepared by subcloning a 12.5 kbp BamH I fragment and inserting a hygromycin resistance gene (from PGKhyg, Te Riele et al., 1990) into the unique SnaB I site located within an exon sequence of Msh2. Cloning procedures were performed according to Sambrook et al. (1989).

The targeting construct was separated from vector sequences by gel electrophoresis, purified by electroelution and introduced into 129OLA-derived ES cell line E14 by electroporation as described (Te Riele et al., 1992). Electroporated cells were seeded onto gelatin-coated 10 cm dishes ($10^7$ cells per plate) and subjected to hygromycin B selection (150 µg per ml) in BRL-conditioned medium (Hooper et al., 1987) the following day. After 10 days, individual hygromycin B-resistant colonies were randomly picked and expanded on mouse embryonic fibroblasts feeder layers. DNA was extracted from expanded colonies, digested with EcoR I and analyzed by Southern hybridization using probes flanking both sides of the targeting construct (FIG. 1A). Two cell lines were obtained out of 135 hygromycin B-resistant colonies showing bands diagnostic for correct integration of the hyg marker between codons 588 and 589 of one copy of the Msh2 gene. These cell lines were designated sMsh2-42 and sMsh2-55. One cell line obtained from this experiment, designated wt-2, carrying a randomly integrated hyg gene, was used as an $Msh2^{+/+}$ control.

To obtain an ES cell line carrying a disruption in both copies of Msh2, $10^6$ cells of cell line sMsh2-55 were plated onto 10 cm plates and cultured in BRL-conditioned medium containing 1.0 or 1.5 mg per ml of hygromycin B. After 12 days of culturing in selective medium and 7 days in non-selective medium, 24 colonies were obtained which had survived 1.5 mg per ml of hygromycin B. DNA was extracted from expanded colonies, digested with EcoR I and analyzed by Southern hybridization. One cell line, designated dMsh2-9, carried two disrupted Msh2 alleles, had lost the wild-type copy and contained the normal number of chromosomes. ES cell lines which had survived 1.0 mg per ml of hygromycin B still contained one disrupted and one wild-type Msh2 copy. One of these $Msh2^{+/-}$ lines was designated sMsh2-21 and used for several experiments. Diploidy of cell lines sMsh2-55 and dMsh2-9 was verified by karyotyping (not shown).

No Msh2 transcript could be detected in ES cell line dMsh2-9 by Northern blotting (not shown), indicating that the hyg marker strongly suppressed Msh2 expression. The genotype of ES cell line dMsh2-9 will therefore be indicated by $Msh2^{-/-}$.

To verify the absence of mismatch repair due to the knockout of both msh2 alleles the mismatch binding activity in the mismatch repair deficient msh-2-/- and wild-type cells was compared.

Two different mismatch-binding activities have been described in mammalian cell extracts using gel-retardation assays:

(i) An activity that recognizes G.T mismatches (Jiricny et al., 1988: Stephenson and Karran, 1989; Griffin and Karran, 1993), an extrahelical T.G dinucleotide (Aquilina et al.; 1994) representing an intermediate in replicational slippage of a microsatellite and, weakly, G.A, G.G, A.C. and G.U mismatches (Stephenson and Karran, 1989: Hughes and Jiricny, 1992).

(ii) In one cell line, an independent activity was detected that recognizes A.C mismatches and also pyrimidine—pyrimidine mismatches (Stephenson and Karran, 1989). Based on protein sequencing, the purified G.T-binding activity was shown to contain MSH2 protein (Palombo, et al., 1994).

To characterize the mismatch binding properties of the Msh2-/- ES cell line, we have performed gel-retardation assays using cell extracts of wild-type ES cell line wt-2 and Msh2-deficient line dMsh2-9.

Gel Shift Assay

Preparation of cell extracts, annealing of oligonucleotides, binding of cell extracts to duplex oligonucleotides containing mismatched or extrahelical nucleotides, and non-denaturing polyacrylamide gel electrophoresis were performed essentially as described (Stephenson and Karran, 1989). However, gel electrophoresis was performed in TAE buffer rather than in TBE buffer. To obtain duplex oligonucleotides, the oligonucleotide U: 5'-GGGAAGCTGC-CAGGCCCCAGTGTCAGCCTCCTATGCTC-3' (SEQ ID NO:1) (sequences were derived from Aquilina et al., 1994) was radiolabeled and annealed with any of the following unlabeled oligonucleotides: L-G.T: 5'GAGCATAGGAG-GCTGACATTGGGGCCTGGCAGCTTCCC-3' (SEQ ID NO:2) (resulting in a G.T mismatch); L-G.A: 5'-GAGCAT-AGGAGGCTGACAATGGGGCCTGGCAGCTTCCCC-3' (SEQ ID NO:3) (resulting in a G.A mismatch); L-G.G: 5'-GAGCATAGGAGGCTGACAGTGGGGCCTG-GCAGCTTCCC-3' (SEQ ID NO:4) (resulting in a G.G mismatch); L-A.C: 5'-GAGCATAGGAGGCTGACAC-CGGGGCCTGGACAGCTTCCC-3' (SEQ ID NO:5) (resulting in an A.C mismatch); L-TG: 5'-GAGCATAGGAG-GCTGACACTGTGGGGCCTGGCAGCTTCCC-3' (SEQ ID NO:6) (resulting in an extrahelical TG dinucleotide); L-HOM: 5'-GAGCATAGGAGGCTGACACTGGGGC-CTGGCAGCTTCCCC-3' (SEQ ID NO:7) (resulting in a homoduplex); L-LOOP14: 5'-GAGCATAGGAGGCTGA-CACATACGTGAGTACTCTGGGGCCTG-GCAGCTTCCC-3' (SEQ ID NO:8) (resulting in an IDL loop of 14 extrahelical nucleotides). In all assays, a twofold excess of unlabeled homoduplex competitor oligonucleotide was included. As a positive control, a duplex oligonucleotide containing the binding site for the E2F family of transcription factors was used (Beijersbergen et al., 1995).

Results of these experiments as shown in FIG. 2 clearly demonstrate binding activity in wild-type cell extracts to a G.T mismatch and to an extrahelical TG dinucleotide. Binding to both oligonucleotides was entirely absent in the extract of the Msh2-/- ES cell line, demonstrating the involvement of the Msh2 protein in this binding activity. As shown before (Hughes and Jiricny, 1992), binding was abolished by the inclusion of ATP in the binding reaction (not shown). We were unable to detect specific binding to G.A., G.G, or A.C mismatches under the conditions used in wild-type or mutant cell extracts. In addition, no Msh-2 dependent binding to a 14-nucleotide IDL was observed (FIG. 2).

Microsatellite Formation

Subclones of ES cell lines dMsh2-9 and wt-2 were generated by seeding cells onto mouse embryonic fibroblasts feeder layers at a density of $10^3$ cells per 10 $cm^2$. At that time, the ES cell lines were in culture for approximately 20 divisions since their generation. Twenty-four colonies from each cell line were expanded. Chromosomal DNA was isolated and subjected to the polymerase chain reaction using two end-labeled primer pairs (D14Mit15 and D7Mit17, Dietrich et al., 1994). Amplified products were electrophoresed on a denaturing polyacrylamide gel.

Whereas none of the wt-2 sublines showed any alteration in microsatellite length, clear length alterations in many dMsh2-9 sublines were seen for both microsatellites (8 out of 24 for marker D7Mit17 and 6 out of 24 for marker D14Mit15, FIG. 3). This observation strongly suggests that the Msh2 protein is involved in the repair of slipped replication intermediates. The microsatellites-slippage rate was estimated to be $10^{-2}$ to $10^{-3}$ per generation.

Mutation Frequency

The effect of loss of the Msh2 gene on the mutation frequency of a functional gene was analysed. To this purpose, $6 \times 10^6$ cells of ES cell lines dmsh2-9 and wt-2 were plated onto 486 cm$^2$ gelatin-coated tissue culture surface in BRL-conditioned medium. After two days, 6-Thioguanine (6-TG) was added at a concentration of 10 μg per ml to select for cells that have lost activity of the X-linked Hprt gene by mutation. After two weeks the number of resistance colonies was counted.

Whereas no 6-TG-resistant colonies were seen in the wt-2 culture, 188 resistant colonies were present in the dMsh2-9 culture. This result extends the mutator phenotype of Msh2−/− cells to functional genes.

Tolerance to N-methyl-N$^1$-nitro-N-nitrosoguanidine (MNNG)

Mismatch Repair (MMR) was suggested to mediate hypersensitivity to agents that methylate G residues at the O$^6$ position. It is believed that MMR recognizes the O$^6$-meG-T misrepair that occurs after erroneous incorporation of a thymidine nucleotide opposite to O$^6$-meG during replication (Griffin et al., 1994). This is supposedly followed by excision and repair synthesis, again incorporating thyamidine opposite to O$^6$-meG, triggering a new round of MMR. The net result of this cycling between excision and resynthesis will be the presence of single-stranded regions at the site of O$^6$-meG which will lead to double-stranded gaps when replicated during S phase, resulting in cell death (for reviews, see Karran and Bignami, 1992; Karran and Bignami, 1994).

It is predicted that loss of MMR will present this process, thus conferring tolerance to simple methylating agents. To test this hypothesis directly, survival of Msh2−/− cell line dMsh2-9, Msh+1− cell line Msh2-21 and wild-type cell line wt-2 was determined after exposure to a range of concentration of N-methyl-N$^1$-nitro-N-nitrosoguanidine (MNNG).

ES cell lines dMsh2-9, sMsh2-21 and wt-2 were seeded onto MEF feeder layers (mouse embryo fibroblast cells) at a density of $10^3$ cells per 4 cm$^3$. The following day, cells were exposed for one hour to MNNG ranging in concentration from 0 to 36.45 μM in serum-free medium. After 4 days of incubation, cells were trypsinized, stained with Trypan blue and counted. During the whole procedure from one hour before exposure to MNNG, O$^6$-benzylguanine (20 μM) was included in the medium in order to competitively inhibit endogenous methyltransfarase activity that might otherwise remove the methyl groups added by MNNG (Dolan et al., 1990).

FIG. 4 shows that the LD$_{50}$ for MNNG was increased 20-fold in the Msh−/− cell line compared to the heterozygous and wild-type cell lines, directly proving the involvement of Msh2 in determining cellular sensitivity to MNNG. Heterozygous cell line sMsh2-21 displayed no increased tolerance to MNNG.

The phenotypic consequences of an Msh2 deficiency in mouse embryonic stem cells provide clear evidence for an essential role of Msh2 in mammalian DNA mismatch repair. First, Msh2-deficient ES cells lack binding activity to a double stranded 38-mer oligonucleotide carrying a G·T mismatch or an unpaired TG dinucleotide. Based on protein sequencing, the purified G.T-binding activity was shown to contain the Msh2 protein (Palombo et al., 1994). To characterize the mismatch binding properties of the Msh2−/− ES cell line, we have performed gel-retardation assays using cell extracts of wild-type ES cell line wt-2 and Msh2-deficient line dMsh2-9. Extracts were incubated with radiolabeled 38-mer double-stranded oligonucleotides containing either a mismatch, an extrahelical dinucleotide, or a 14-nucleotide insertion-deletion-type loop (IDL), followed by electrophoresis on a nondenaturing polyacrylamide gel. Results of these experiments as shown in FIG. 2 clearly demonstrate binding activity in wild-type cell extracts to a G.T mismatch and to an extrahelical TG dinucleotide. Binding to both oligonucleotides was entirely absent in the extract of the Msh2−/− ES cell line, demonstrating the involvement of the Msh2 protein in this binding activity. As shown before (Hughes and Journey, 1992), binding was abolished by the inclusion of ATP in the binding reaction (not shown). We were unable to detect specific binding to G.A, G.G, or A.C mismatches under the conditions used in wild-type or mutant cell extracts. In addition, no Msh2-dependent binding to a 14-nucleotide IDL was observed (FIG. 2).

Second, Msh2-deficient ES cells have a mutator phenotype as evidenced by an at least 150-fold increase in the number of cells resistant to 6-thioguanine, indicating mutational inactivation of the X-linked Hprt gene. Moreover, microsatellite length instability was observed in subclones derived from the Msh2-deficient ES cell line, but not in subclones derived from wild-type ES cells. Whereas none of the wt-2 sublines showed any alteration in microsatellite length, clear length alterations in many dMsh2-9 sublines were seen for both microsatellites (8 out of 24 for maker D7Mit17 and 6 out of 24 for marker D14Mit15, FIG. 3). This observation strongly suggests that the Msh2 protein is involved in the repair of slipped replication intermediates. The microsatellite-slippage rate was estimated to be $10^{-2}$ to $10^{-3}$ per generation. We subsequently investigated the effect of loss of the Msh2 gene on the mutation frequency of a functional gene. To this purpose, $6 \times 10^6$ cells of cell lines wt-2 and dMsh2-9 were plated in the presence of 6-thioguanine (6-TG) to select for cells that have lost activity of the X-linked Hprt gene by mutation. Whereas no 6-TG-resistant colonies were seen in the wt-2 culture, 188 resistant colonies were present in the dMsh2-9 culture. This result extends the mutator phenotype of Msh2−/− cells to functional genes.

Third, Msh2-deficient ES cells resisted a 20-fold higher concentration of the methylating agent N-Methyl-N'-Nitro-N-Nitrosoguanidine than wild-type ES cells. MMR was suggested to mediate hypersensitivity to agents that methylate G residues at the O$^6$ position. It is believed that MMR recognizes the O$^6$-meG.T mispair that occurs after erroneous incorporation of a thymidine nucleotide opposite to O$^6$-meG during replication (Griffin et al., 1994). This is supposedly followed by excision and repair synthesis, again incorporating thymidine opposite to O$^6$-meG, triggering a new round of MMR. The net result of this cycling between excision and re-synthesis will be the presence of single-stranded regions at the site of O$^6$-meG residues which will lead to double-stranded gaps when replicated during S phase, resulting in cell death (for reviews, see Karran and Bignami, 1992; Karran and Bignami, 1994).

It is predicted that loss of MMR will prevent this process, thus conferring tolerance to simple methylating agents. To test this hypothesis directly, survival of Msh2−/− cell line dMsh2-9, Msh+/− cell line Msh2-21 and wild-type cell line wt-2 was determined after exposure to a range of concentrations of N-methyl-N'-nitro-N-nitrosoguanidine (MNNG).

In the growth medium, O$^6$-benzylguanine was included to competitively inhibit endogenous methyltransferase activity that might otherwise remove the methyl groups added by MNNG (Dolan et al., 1990). FIG. 4 shows that the $LD^{50}$ for MNNG was increased 20-fold in the Msh2−/− cell line compared to the heterozygous and wild-type cell lines, directly proving the involvement of Msh2 in determining cellular sensitivity to MNNG. Heterozygous cell line sMsh2-21 displayed no increased tolerance to MNNG.

Fourth, mice bred to homozygosity for the disrupted Msh2 allele, originally generated in ES cells, were highly predisposed to tumorigenesis. In E. coli (Shen and Huang, 1986), Drosophila (Nassif and Engels, 1993) and mammalian cells (Waldman and Liskay, 1988, Te Riele et al., 1992), the efficiency of recombination between homologous DNA stretches is highly dependent on their sequence identity. We have previously demonstrated that in a gene targeting assay, homologous recombination at the Retinoblastoma (Rb) locus in ES cells, derived from mouse strain 129, was 50-fold more efficient with a 129-derived targeting construct than with a construct derived from a non-isogenic (BALB/c) mouse strain (Te Riele et al., 1992; Table 1). This construct contained 0.6% base sequence divergence with respect to the isogenic 129 construct. To provide additional evidence that suppression of recombination was solely dependent on the polymorphisms between the endogenous locus and the targeting DNA, we performed the inverse experiment, i.e. targeting of a BALB/c-derived ES cell line with the 129- and BALB/c-derived constructs.

This experiment yielded the inverse result, i.e. a higher targeting efficiency with the BALB/c targeting construct than with the non-isogenic 129 targeting construct (Table 1). To investigate whether MMR is responsible for this anti-recombination effect, we have repeated the Rb targeting experiment in the (129-derived) ES cell line dMsh2-9. We found that in the Msh2−/− cell line homologous recombination at the Rb locus with the non-isogenic construct was as efficient as with the isogenic construct (Table 1). This experiment demonstrates that Msh2 is involved in preventing homologous recombination between diverged DNA sequences.

To study the effect of MMR deficiency on the development of cancer, Msh2+/−ES cell lines sMsh2-55 and sMsh2-42 and Msh2−/− ES cell line dMsh2-9 were used to generate chimeric mice. Both the Msh2 single and double knock-out ES cells gave rise to healthy animals with coat-color chimerism of 20 to 70%. This result suggests that MMR deficiency did not alter the capacity of the ES cells to compete with wild-type cells in chimeric development.

Msh2+/− chimeras were found to transmit the mutant allele through the germ line resulting in Msh2 heterozygous FI mice. These mice, which may serve as a model for HNPCC, were healthy up to at least 8 months of age (Table 2). Intercrossing of Msh2+/− mice resulted in Msh2−/− mice according to a normal Mendelian distribution: they were healthy at birth and fertile. However, 30% of the Msh2−/− mice developed metastasizing lymphomas of T-cell origin with a peak at 2 months of age (Table 2). In addition, one mouse suffered from generalized histiocytic sarcoma at 3.5 months of age. Extensive histological analyses of these mice did not reveal any other abnormality. Also healthy Msh2−/− mice sacrificed at 2 months of age were histologically normal and had normal B- and T-cell populations as evidenced by FACS analysis.

Accordingly, disruption of Msh2 leads to inactivation of mammalian DNA mismatch repair.

By using a gene targeting assay, we demonstrated that it is the mammalian DNA mismatch repair system which is responsible for suppressing homologous recombination between sequences differing as little as 0.6% at the nucleotide level. As described above, homologous recombination at the Rb locus with an isogenic DNA targeting construct was 50-fold more efficient than with a similar, but nonisogenic construct containing on the average 0.6% sequence divergence with respect to the target locus (Te Riele, H. et al., 1992). However, in Msh2-deficient ES cells, homologous recombination at Rb with the nonisogenic targeting construct was as efficient as with the isogenic construct.

Recombination of Diverged Sequences

In E. coli (Shen and Huang, 1986), Drosophila (Nassif and Engels, 1993) and mammalian, cells (Waldman and Liskay, 1988, Te Riele et al., 1992), the efficiency of recombination between homologous DNA stretches is highly dependent on their sequence identity. We have previously demonstrated that in a gene targeting assay, homologous recombination at the Retinoblastoma (Rb) locus in ES cells, derived from mouse strain 129, was 50-fold more efficient with a 129-derived targeting construct than with a construct derived from a non-isogenic (BALB/c) mouse strain (Te Riele et al., 1992; Table 1). This construct contained 0.6% base sequence divergence with respect to the isogenic 129 construct. To provide additional evidence that suppression of recombination was solely dependent on the polymorphisms between the endogenous locus and the targeting DNA the inverse experiment, i.e. targeting of a BALB/c-derived ES cell line with the 129- and BALB/c-derived constructs was performed.

Targeting and subsequent analysis of the Rb locus in a BALB/c-derived ES cell line (kindly provided by S. Rastan) and 129/OLA-derived ES cell lines dMsh2-9 were performed essentially as described (Te Riele et al., 1992). The targeting constructs 129Rb-neo (derived from the 129OLA genome) and B/cRb-neo (derived from the BALB/c genome) carry an insertion of the pMClneo marker in exon 19 of the Rb gene and differ approximately 0.6% at the nucleotide level (Te Riele et al., 1992).

TABLE 1

Homologous recombination has lost dependence on sequence identity in Msh2 deficient ES cells.

| ES cells | Homologous recombination vs total no. G418$^R$ col. with | | Isogenic vs non-isogenic |
|---|---|---|---|
| | 129Rb-nec | B/cRb-neo | |
| BALB/c (Msh2+/+) | 1/68 (1.5%) | 16/72 (22%) | 15 x |
| 129OLA (Msh2+/+) | 33/94 (35%) | 1/144 (0.7%) | 50 x |
| 129OLA (Msh2−/−) | 42/185 (23%) | 47/184 (26%) | 0.9 x |

129Rb-neo and B/cRb-neo are Rb targeting constructs, prepared from the 129 and BALB/c strains of mice, respectively, with 0.6% sequence divergency. Targeting frequencies in 129OLA (Msh2+/+) ES cells are derived from te Riele et al., 1992.

This experiment yielded a higher targeting efficiency with the BALB/c targeting construct than with the non-isogenic 129 targeting construct. To investigate whether MMR is responsible for this antirecombination effect, we have repeated the Rb targeting experiment in the (129-derived) ES cell line dMsh2-9 (Msh−/−). We found that in the Msh2−/− cell line homologous recombination at the Rb locus with the non-isogenic construct was as efficient as with the isogenic construct (Table 1). This experiment demonstrates that Msh2 is involved in preventing homologous recombination between diverged DNA sequences.

This finding provides a method for modifying the mammalian genome via homologous recombination. By knockout of the msh2 gene and thus inactivating the mismatch repair system targeted recombination can be achieved despite divergence in the target locus that otherwise prevents recombination in a mismatch repair sufficient background.

Phenotype of Msh −/− Mice

Chimeric mice were obtained by injecting 10–15 cells of ES cell lines sMsh2-55, sMsh2-42 and dMsh2-9 into C57B1/6 blastocysts. Male chimeras obtained with Msh2+/− ES cells were crossed with wild-type 1290LA and FYB mice and found to transmit the mutated Msh2 allele through the germ line. Homozygous Msh2 mutant mice were obtained by intercrossing FI heterozygotes. Both the Msh2 single and double knock-out ES cells gave rise to healthy animals with coat-color chimerism of 20 to 70%. This result evidences that MMR deficiency did not alter the capacity of the ES cells to compete with wild-type cells in chimeric development.

Msh2+/− chimeras were found to transmit the mutant allele through the germ line resulting in Msh2 heterozygous F1 mice. These mice were healthy up to at least 8 months of age (Table 2).

Intercrossing of Msh2+/− mice resulted in Msh2−/− mice according to a normal Mendelian distribution; they were healthy at birth and fertile. However, 30% of the Msh2−/− mice developed metastasizing lymphomas of T-cell origin with a peak at 2 months of age (Table 2). In addition, one mouse suffered from generalized histiocytic sarcoma at 3.5 months of age. Extensive histological analyses of these mice did not reveal any other abnormality. Also healthy Msh2−/− mice sacrificed at 2 months of age were histologically normal and had normal B- and T-cell populations as evidenced by FACS analysis.

TABLE 2

Phenotypes of Msh2 mutant mice.

| Genotype | Age (months) | Condition at birth | Tumor incidence type | frequency** | age (months) |
|---|---|---|---|---|---|
| Msh2+/− | 8 | healthy | | 0/110 | |
| Msh2+/+::Msh2−/−* | 6 | healthy | Lymphoma | 1/24 | 2 |
| Msh2−/− | 4–5 | healthy | Lymphoma | 6/19 | 2–4 |
| | | | Histiocytic sarcoma | 1/19 | 3.5 |

*Chimeras consisting of wild-type and Msh2−/− cells
**Number of mice carrying a tumor per total number in the experiment

BIBLIOGRAPHY

Aaltonen, L. A., Peltomaki, P., Mecklin. J.-P., Jarvinen, H., Jass, J. R., Green, J. S., Lynch. H. T., Watson, P., Tallqvist, G., Juhola. M., Sistonen, P., Hamilton, S. R., Kinzier, K. W., Vogelstein. B., and de la Chapelle, A. (1994) Replication errors in benign and malignant tumors from hereditary nonpolyposis colorectal cancer patients. Cancer Res. 54, 1645–1648.

Alani, E., Chi. N.-W., and Kolodner, R. (1995). The *Saccharomyces cerevisiae* Msh2 protein specifically binds to duplex oligonucleotides containing mismatched DNA base pairs and insertions. Genes Development 9, 234–247.

Alani, E., Reenan, R. A. G., and Kolodner, R. D. (1994). Interaction between mismatch repair and genetic recombination in *Saccharomyces cerevisiae*. Genetics 137, 19–39.

Aquilina, G., Biondo, R., Doglotti, E., and Bignami, M. (1993). Genetic consequences of tolerance to methylation DNA damage in mammalian cells. Carcinogenesis 14, 2097–2103.

Aquilina, G., Hess, P., Branch, P., MacGeoch, C., Casciano, I., Karran, P., and Bignami, M. (1994). A mismatch recognition defect in colon carcinoma confers DNA microsatellite instability and a mutator phenotype. Proc. Natl. Acad. Sci. USA 91, 8905–8909.

Askew, G., Doetchman, T, and Lingrel, J. (1993) Mol. Cell. Biol. 13, 4115–4124.

Beijersergen, R. L., Carlée, L., Kerkhoven, R. M., and Bernards, R. (1995). Regulation of the retinoblastoma protein-related p107 by G1 cyclin complexes. Genes Development in press.

Bhattacharyya, N. P., Skandalis, A., Ganesh, A., Groden, J., and Meuth, M. (1994). Mutator phenotypes in human colorectal carcinoma cell lines. Proc. Natl. Acad. Sci. USA. 91, 6319–6323.

Bicknell, D. C., Rowan, A., and Bodmer, W. F. (1994). βM-microglobulin gene mutations: a study of established colorectal cell lines and fresh tumors. Proc. Natl. Acad. Sci. USA 91, 4751–4755.

Bouffler, S., Silver, A., and Cox, G. (1993). The role of DNA repeats and associated structures in genomic instability and neoplasia. BioEssays 15, 409–412.

Branch, P., Aquilina, G., Bignami, M., and Karran, P. (1993). Defective mismatch binding and a mutator phenotype in cells tolerant to DNA damage. Nature 362, 652–654.

Bronner, C. E., Baker, S. M., Morrison, P. T., Warren, G., Smith. L. G., Lescoe, M. K., Kane, M., Earabino, C., Lipford, J., Lindblom, A., Tannergard, P. m Bollag, R. J., Godwin, A. R., Ward, D. C., Nordenskjold, M., Fishel, R., Kolodner, R., and Liskay, R. M. (1994). Mutation in the DNA mismatch repair gene homologue hMLH1 is associated with hereditary non-polyposis colon cancer. Nature 368, 258–261.

Brosius, J., and Gould, S. J. (1992). On "genomenclature": a comprehensive (and respectful) taxonomy for pseudogenes and other "junk DNA". Proc. Natl. Acad. Sci. USA 89, 10706–10710.

Camerini-Otero, R. D., and Kucherlapati, R. (1990) The New Biologist 2, 337–341.

Capecchi, M. (1989) Science 244, 1288–1292.

Chong, J.-M., Fukayama. M., Hayashi, U. Takiawa, T., Koike, M., Konishi, M., Kiuchi-Yanoshita, R., and Miyaki, M. (1994). Microsatellite instability in the progression of gastric carcinoma. Cancer Research 54, 4595–4597.

Claverys, J. P., and Lacks, S. A. (1986) Microbiol. Rev. 50, 133–165.

Cohen, P. R., Kohn, S. R., and Kurzrock, R. (1991). Association of sebaceous gland rumours and internal malignancy: the Muir-Torre syndrome. Am. J. Med. 90, 606–613.

Cruz, A., and Beverly, S. M. (1990) Nature 348, 171–173.

Deng, C., and Capecchi, M. (1992) Mol. Cel. Biol. 12, 3365–3371.

Dietrich, W. F., Miller, J. C., Steen, R. G., Merchant, M., Damron, D., Nahf, R., Gross, A., Joyce, D. C., Wessel, M., Dredge, R. D., Marquis, A., Stein, L. D., Goodman, N., Page, D. C., and Lander, E. C. (1994). A genetic map of the mouse with 4,006 simple sequence length polymorphisms. Nature Genetics 7, 220–240.

Dolan, M. E., Moschel, R., and Pegg, A. E. (1990). Depletion of mammalian $O^6$-alkylguanine-DNA alkyltransferase activity by o6-benzylguanine provides a means to evaluate the role of this protein in protection against carcinogenic and therapeutic alkylating agents. Proc. Natl. Acad. Sci. USA 87, 5368–5372.

Eshleman, J. R., Lang, E. Z., Bowerfind, G. K., Parsons, R., Vogelstein, B., Wilison, J. K. V., Veigl, M. L., Sedwick, W. D., and Markowitz, S. D. (1995). Increased mutation rate at the hprt locus accompanies microsatelite instability in colon cancer. Oncogene 10, 33–37.

Fang, W., and Modrich, P. (1993). Human strand-specific mismatch repair occurs by a bidirectional mechanism similar to that of the bacterial reaction. J. Biol. Chem. 268, 11338–11844.

Fishel, R., Ewel, A., and Lescoe, M. K. (1994). Purified human MSH2 protein binds to DNA containing mismatched nucleotides. Cancer Res. 54, 5539–5542.

Fishel, R., Ewel, A., Lee, S., Lescoe, M. K., and Griffith, J. (1994). Binding of mismatched microsatellite DNA sequences by the human MSH2 protein. Science 266, 1403–1405.

Fishel, R., Lescoe, M. K., Rao, M. R. S., Copeland. N. G., Jenkins, N. A., Garber, J., Kane, M., and Kolodner, R. (1993). The human mutator gene homolog MSH2 and its association with hereditary nonpolyposis colon cancer. Cell 75, 1027–1033.

Frohman, M. A., and Martin, G. R. (1989) Cell 56, 145–147.

Goldmacher, V S., Cuzick, Jr., R. A., and Thilly, W., G. (1986). Isolation and partial characterization of human cell mutants differing in sensitivity to killing and mutation by methylnitrosourea and N-methyl-N'-nitro-N-nitrosoguanidine. J. Biol. Chem. 261, 12462–12471.

Griffin, S., and Karran, P. (1993). Incision at DNA G.T mispairs by extracts of mammalian cells occurs preferentially at cytosine methylation sites and is not targeted by a separate G.T binding reaction. Biochemistry 32, 13032–13039.

Griffin, S., Branch, P., Xu, Y.-Z., and Karran, P. (1994). DNA mismatch binding and incision at modified guanine bases by extracts of mammalian cells: Implications for tolerance to DNA methylation damage. Biochemistry 33, 4737–4793.

Han, H.-J., Yanagisawa, A., Kato, Y., Park, J.-G., Nakarriura, Y. (1993). Genetic instability in pancreatic cancer and poorly differentiated type of gastric cancer. Cancer Research 53, 5087–5089.

Hanson, K. D., and Sedivy, J. M. (1995) Mol. Cel. Biol. 15, 45–51.

Hansen, M. F., and Cavenee, W. K. (1988) Trends Genet. 4, 125–128.

Hartwell, L. (1992). Defects in a cell cycle checkpoint may be responsible for the genomic instability of cancer cells. Cell 71, 543–546.

Hasty, P. et al. (1993) Nature 350, 243–246.

Hemminki, A., Peltomaki, F, Mecklin, J.-P., Järvinen, H., Salovaara. R., Nysrom-Lahti, M, de la Chapelle, A., and Aaltonen, L. A. (1994). Loss of the wild type MLHI gene is a feature of hereditary nonpolyposis colorectal cancer. Nature Genetics 8, 405–410.

Hogan, B., Beddington, R., Constantini, F., and Lacy, E. (1994) Manipulating the mouse embryo, $2^{nd}$ edition, Cold Spring harbor Laboratory Press, Plainview, N.Y.

Holmes Jr., J., Clark, S., and Modrich, P. (1990). Strand-specific mismatch correction in nuclear extracts of human and *Drosophila melanogaster* cell lines. Proc. Natl. Acad. Sci. USA. 87, 5337–5841.

Hooper, M., Hardy, K., Handyside, A., Hunter, S., and Monk, M. (1987). HPRT-deficient (Lesh-Nyhan) mouse embryos derived from germline colonization by cultured cells. Nature 326, 292–295.

Hughes, M. J., and Jiricny, J. (1992). The purification of a human mismatch-binding protein and association of its associated ATPase and helicase activities. J. Bid. Chem. 267, 23876–23882.

Jass, J. R., Stewart, S. M., Stewart, J., and Lane, M. R. (1994). Hereditary non-polyposis colorectal cancer: morphologies, genes and mutations. Mutat. Res. 310, 125–133.

Jiricny, J. (1994). Colon cancer and DNA repair: have mismatches met their match? Trends in Genetics 10, 164–168.

Jiricny, J., Hughes, M., Corman, N., and Rudkin, B. B. (1988). A human 200-kDa protein binds selectively to DNA fragments containing G.T mismatches. Proc. Natl. Acad. Sci. USA 85, 8860–8864.

Karran, P., and Bignami, M. (1992). Self-destruction and tolerance in resistance of mammalian cells to alkylation damage. Nucl. Acids Res. 20, 2933–2940.

Karran, P., and Bignami, M. (1994). DNA damage tolerance, mismatch repair and genome instability. BioEssays 16, 833–839.

Kat, A., Thilly W. G. Fang, W.-H., Longley, M. J., Li, G.-M., and Modrich, P. (1993). An alkylation-tolerant, mutator human cell line is deficient in strand-specific mismatch repair. Proc. Natl. Acad. Sci. USA 90, 6424–6428.

Kilby, N., Snaith, M., and Murray, J. (1993) Trends Genet. 9, 413–421.

Koi, M., Umar, A., Chauhan, D. P., Cheman, S. P., Carethers. J. M., Kunkel, T. A., and Boland, C. R. (1994). Human chromosome 3 corrects mismatch repair deficiency and microsatellite instability and reduces N-methyl-N'-nitro-N-nitrosoguanidine tolerance in colon tumor cells with homozygous hMLH1 mutation. Cancer Research 54, 4308–4314.

Kolodner, R, D., Hall. N. R., Lipford, S., Kane, M. F., Rao, M. R. S., Morrison, P., Wirth, L., Finan, P. J., Burn, J., Chapman. P., Earabino, C., Merchant, E., and Bishop, D.

T. (1994). Structure of the human MSH2 locus and analysis of two Muir-Torre kindreds for msh2 mutations. Genomics 24, 516–526.

Kolodner, R. D., Hall, N. R., Lipford. J., Kane, M. F., Morrison, P., Wirth, L., Finan, P. S., Burn, J., Chapman, P., Earabino, C., Merchant, E., and Bishop, D. T. (1995). Structure of the human MLH1 locus and analysis of a large hereditary nonpolyposis colorectal carcinoma kindred for mlh 1 mutations. Cancer Res. 55, 242–248.

Kramer, B., Kramer, W., Williamson, M., and Fogel, S. (1989). Heteroduplex DNA correction in *Saccharomyces cerevisiae* is mismatch specific and requires functional PMS genes. Mol. Cell. Biol. 9, 4432–4440.

Kramer, W., Kramer, B., Williamson, M. S., and Fogel, S. (1989). Cloning and nucleotide sequence of DNA mismatch repair gene PMS1 from *Saccharomyces cerevisiae*: homology of PMS1 with procaryotic MutL and Hex. B. S. Bacteriology 171, 5339–5346.

Kucherlapati, R., and Smith, G. R., eds. (1988) Genetic Recombination. American Society for Microbiology, Washington.

Lazar, V., Grandjouan, S. Bognel, C., Couturier, D., Rougier, P., Bellet, D., and Bressacde Paillerets, B. (1994). Accumulation of multiple mutations in tumour suppressor genes during colorectal tumorigenesis in HNPCC patients. Hum. Mol. Genet. 3, 2257–2260.

Leach, F. S., Nicolaides, N. C., Papadopoulos, N., Liu, B., Jen, J., Parsons, R., Peltomaki, P., Sistonen, P., Aaltonen, L. A. Nystrom-Lahti, M., Guan, X.-Y., Zhang, L., Meltzer, P. S., Yu, J.-W., Kao, F.-T., Chen, D. J., Cerosaletti, K. M., Fournier, R. E. K., Todd, S., Lewis, T., Leach, R. J., Naylor, S. L., Weissenbach, J., Mecklin, J.-P., Järvinen, H., Petersen, G. M., Hamilton, S. R., Green. J., Jass, J., Watson, P., Lynch, H. T., Trent, S. M., de la Chapelle, A., Kinzler, K. W., and Vogeistein. B. (1993). Mutations of mutS homolog in hereditary nonpolyposis colorectal cancer. Cell 75, 1215–1225.

Li, G.-M., and Modrich, P. (1995). Restoration of mismatch repair to nuclear extracts of H6 colorectal tumor cells by a heterodimer of human MutL homologs. Proc. Natl. Acad. Sci. USA 92, 1950–1954.

Liu, B., Nicolaides, N. C., Markowitz, S., Willson, J. K. V., Parsons, R. E., Jen, S., Papadopoulos, N., Peltomäki, P., de la Chapelle, A., Hamilton, S. R., Kinzler, K. W., and Vogeistein, B. (1995). Mismatch repair gene defects in sporadic colorectal cancers with microsatellite instability. Nature Genetics 9, 48–55.

Liu, B., Parsons, R. E., Hamilton, S. R., Petersen, G. M., Lynch, H. T., Watson. P., Markowitz, S., Willson, J. K. V., Green, J., de la Chapelle, A., Kinzler, K. W., and Vogelstein, B. (1994). hMSH2 mutations in hereditary nonpolyposis colorectal cancer kindreds. Cancer Research 54, 4590–4594.

Loeb, L. A. (1994). Microsatellite instability: marker of a mutator phenotype in cancer. Cancer Research 54, 5059–5063.

Lynch, H. T., Smyrk, T. C., Watson, P., Lanspa, S. S., Lynch, J. F., Cavalieri, R. J., and Bolland, C. R. (1993). Genetics, natural history. tumor spectrum, and pathology of hereditary nonpolyposis colorectal cancer: an updated review. Gastroenterology 104, 1535–1549.

Malkin et al. (1990) Science 250, 1233–1238.

Michejda, C. J., Smith, Jr., R. H., and Kroeger Koepke, M. B. (1994). DNA alkylation by triazenes and related compounds. In DNA adducts: identification and biological significance, K. Hemminki, A. Dipple, D. E. G. Shuker, F. Kadlubar, D. Segerbäck, and H. Bartsch, eds. (IARC scientific publications and Oxford University press), pp. 323–337.

Miret, J. J., Mila, M. G., and Lahue, R. S. (1993). Characterization of a DNA mismatchbinding activity in yeast extracts. J. Biol. Chem. 268, 3507–3513.

Mironov, N. M., Aguelon, M. A.-M., Potapova, G. I., Omori, Y., Gorbunov, G. V., Klimenkov, A. A., and Yamasaki, H. (1994). Alterations of $(CA)_n$ repeats and tumor suppressor genes in human gastric cancer. Cancer Res. 54, 41–44.

Modrich, P. (1991). Mechanisms and biological effects of mismatch repair. Annu. Rev. Genet. 25, 229–253.

Modrich. P. (1994). Mismatch repair. genetic stability, and cancer. Science 266, 1959–1960.

Mortensen, R. M., Conner, D. A., Chao, S., Geisterfer-Lowrance, A. A. T., and Seidman, J. G. (1992). Production of homozygous mutant ES cells with a single targeting construct. Mol. Cell. Biol. 12, 2391–2395.

Nassif, N., and Engels. W. (1993). DNA homology requirements for mitotic gap repair in *Drosophila*. Proc. Natl. Acad. Sci. USA 90, 1262–1266.

Nicolaides, N. C., Papadopoulos, N., Liu, B., Wei, Y.-F., Carter. K.-C. Ruben, S. M., Rosen, C. A., Haseltine, W. A., Fleischmann, R. D., Fraser, C. M., Adams M. D., Venter, J. C., Dunlop. M. G., Hamilton, S. R., Petersen, G. M., de la Chapelle, A., Vogelstein., B., and Kinzler, K. W. (1994). Mutations of two PMS homologues in hereditary nonpolyposis colon cancer. Nature 371, 75–80.

Nowak, R. (1994). Mining treasures from 'junk DNA'. Science 263, 608–610.

Orth, K., Hung, S., Gazdar, A., Bowcock, A., Mathis, J. M., and Sambrook, J. (1994). Genetic instability in human ovarian cancer cell lines. Proc. Natl. Acad. Sci. USA. 91, 9495–9499.

Palombo, F., Hughes, M., Jiricny, J., Truong, O., and Hsuan, J. (1994). Mismatch repair and cancer. Nature 367, 417.

Papadopoulos, N., Nickolaides, N. C., Wei, Y.-F., Ruben, S. M., Carter, K. C., Rosen, C. A., Haseltine, W. A., Fleischmann, R. D., Fraser, C. M., Adams, M. D., Venter, J. C., Hamilton, S. R., Petersen, G. M., Watson, P., Lynch, H. T., Peltomaki. P., Mecklin, J.-P., de la Chapelle, A., Kinzler, K. W., and Vogelstein, B. (1994). Mutation of mutL homolog in hereditary colon cancer. Science 263, 1625–1629.

Parsons, R., Li, C.-M., Longley, M., Modrich, P., Liu, B., Beck, T., Hamilton, S. R., Kinzier, K. W., and Vogeistein, B. (1995). Mismatch repair deficiency in phenotypically normal human cells. Science 268, 738–740.

Parsons, R., Li. O.-M., Longley. M. S., Fang, W., Papadopoulos, M., Jen, S., de la Chapelle, A., Kinzler. K. W., Vogelstein. B., and Modrich, P. (1993). Hypermutability and mismatch repair deficiency in RER$^+$ tumor cells. Cell 75, 1227–1235.

Petit, M. A., Dimpfl, S., Radman, M., and Echols, H. (1991). Control of large chromosomal duplications in *Escherichia coli* by the mismatch repair system. Genetics 129, 327–332.

Prolla, T. A., Christie, D.-M., and Liskay, R. M. (1994). Dual requirement in yeast DNA mismatch repair for MLHI and PMS1, two homologs of the bacterial mutL gene. Mol. Cell. Biol. 14, 407–415.

Prolla, T., Pang, Q., Alani, E., Kolodner, R. D., and Liskay, R. M. (1994). MLH1, PMS 1, and MSH2 interactions during the initiation of DNA mismatch repair in yeast. Science 265, 1091–1093.

Rayssiguier, C., Thaler, D. S. and Radman, M. (1989). The barrier to recombination between *Escherichia coli* and Salmonella typhimurium is disrupted in mismatch-repair mutants. Nature 342, 396–401.

Reenan, R. A. G., and Kolodner, R. (1992a). Isolation and characterization of two Saccharomyces cerevisiae genes encoding homologs of the bacterial HexA and MutS mismatch repair proteins. Genetics 132, 963–973.

Reenan, R. A. G., and Kolodner, R. (1992b). Characterization of insertion mutations in the Saccharomyces cerevisiae MSH1 and MSH2 genes: evidence for separate mitochondrial and nuclear functions. Genetics 132, 975–985.

Risinger, J. I., Berchuck, A., Kohier, M. F., Watson, P., Lynch, H. T., and Boyd, J. (1993). Genetic instability of microsatellites in endometrial carcinoma. Cancer Res. 53, 5100–5103.

Sambrook, J., Fritsch, E. F., and Maniatis, T. (1989). Molecular cloning, a laboratory manual, 2nd. edition. Cold Spring Harbor Laboratory Press. Selva, E., New, L., Crouse, G., and Lahue, R. S. (1995). Mismatch correction acts as a barrier to homeologous recombination in Saccharomyces cerevisiae. Genetics 139, 1175–1188.

Schen, P., and Huang, H. V. (1986). Homologous recombination in Escherichia coli: Dependence on substrate length and homology. Genetics 112, 441–457.

Shibata, D., Peinado, M. A., Ionov, Y., Malkhosyan, S., and Perucho, M. (1994). Genomic instability in repeated sequences is an early somatic event in colorectal tumorigenesis that persists after transformation. Nature Genetics 6, 273–281.

Stephenson, C., and Karran, P. (1989). Selective binding to DNA base pair mismatches by proteins from human cells. J. Biol. Chem. 264, 21177–21182.

Strand, M., Prolla. T. A., Liskay, R. M., and Petes, T. D. (1993). Destabilization of tracts of simple repetitive DNA in yeast by mutations affecting DNA mismatch repair. Nature 365, 274–276.

Sulston, J. E., and Horvitz, H. R. (1977) Devi Biol. 56, 110–156.

Suzuki, H., Harpaz, N., Tarmin, L., Yin, J., Bell, J. D., Hontanosas, M., Groisman. G. M., Abraham, S. M., and Meltzer, S. J. (1994). Microsatellite instability in ulcerative colitis-associated colorectal dysplasias and cancers. Cancer Res. 54, 4841–4844.

Te Riele, H., Robanus Maandag, E., and Berns, A. (1992). Highly efficient gene targeting in embryonic stem cells through homologous recombination with isogenic DNA constructs. Proc. Natl. Acad. Sci. USA 89, 5128–5132.

Te Rilee, H., Robanus Maandag, E., Clarke, A., Hooper, M., and Berns, A. (1990). Consecutive inactivation of both alleles of the pim-1 proo-oncogene by homologous recombination in embryonic stem cells. Nature 348, 649–651.

Ten Asbroek, A., Ouellette, M., and Borst, P. (1990) Nature 348, 174–175.

Thomas, D. C., Roberts, J. D., and Kunkel, T. A. (1991). Heteroduplex repair in extracts of human HeLa cells. J. Biol. Chem. 266, 3744–3751.

Thomas, K. R., and Capecchi, M. R. (1987) Cell 51, 503–512.

Umar, A., Boyer, J. C., and Kunkel, T. A. (1994a). DNA loop repair by human cell extracts. Science 266, 814–816.

Umar, A., Boyer, S. C., Thomas, D. C., Nguyen, D. C., Risinger, J. I., Boyd, S., Ionov, Y., Perucho, M., and Kunkel, T. A. (1994b). Defective mismatch repair in extracts of colorectal and endometrial cancer cell lines exhibiting microsatellite instability. J. Biol. Chem. 269, 14367–14370.

Varlet, I., Radman, M., and Brooks, P, (1990). DNA mismatch repair in Xenopus egg extracts: Repair efficiency and DNA repair synthesis for all single base-pair mismatches. Proc. Natl. Acad. Sci. USA 87, 7883–7887.

Valet, I., Pallard, C., Radman, M., Moreau, S., and de Wind, N. (1994). Cloning and expression of the Xenopus and mouse Msh2 DNA mismatch repair genes. Nucl. Acids. Res. 22, 5723–5728.

Vogelstein, B., and Kinzier, K. (1993). The multistep nature of cancer. Trends in Bioch. Sci. 9, 138–141.

Wada, C., Shionoya, S., Fujino, Y., Tokuhiro, H., Akahoshi, T., Uchida, T., and Ohtani, H. (1994). Genomic instability of microsatellite repeats and its association with the evolution of chronic myelogenous leukemia. Blood 83, 3449–3456.

Waldman, A. S., and Liskay, R. M. (1988). Dependence of intrachromosomal recombination in mammalian cells on uninterrupted homology. Mol. Cell. Biol. 8, 5350–5357.

Watson J. E., Slorach E. M., Maule J., Lawson D., Porteous D. J., and Brookes A. J. (1995) Human repeat-mediated integration of selectable markers into somatic cell hybrids. Genome Res. 5, 444–452

Wooster, R., Cleton-Jansen, A.-M., Collins, N., Mangion, J., Cornelis, R. S., Cooper, C. S., Gusterson, B. A. Ponder, B. A. J., von Deimling, A., Wiestler, O. D., Cornelisse, C. J. Devilee, P., and Stratton, M. R. (1994). Instability of short tandem repeats (microsatellites) in human cancers. Nature Genetics 6, 152–156.

Worth, Jr., L., Clark, S., Radman, M., and Modrich, P. (1994). Mismatch repair proteins MutS and MutL inhibit RecA-catalyzed strand transfer between diverged DNAs. Proc. Natl. Acad. Sci. USA 91, 3238–3241.

Young, J., Leggett, B., Gustafson, C., Ward, M., Searle, J., Thomas, L., Buttenshaw, R., and Chevenix-Trench, G., (1993). Genomic instability occurs in colorectal carcinomas but not in adenomas. Human Mutation 2, 351–353.

The invention claimed is:

1. A diploid mammalian cell made by making a mammalian cell having a mismatch repair deficiency phenotype, comprising inactivating the mismatch repair system of the mammalian cell by disrupting both copies of a gene essential for mismatch repair, wherein both Msh2 alleles are inactivated and the cell is a dMsh2-9 mouse embryonic stem cell (ATCC deposit number RH532).

2. A method for stably incorporating through homologous recombination a donor DNA molecule into the genome of a mammalian recipient cell, wherein the recipient cell is the cell of claim 1, comprising transforming the recipient cell having a mismatch repair deficiency phenotype with a donor DNA molecule that is obtained from a donor cell, wherein the donor DNA molecule is stably integrated into the genome of the recipient cell through homologous recombination with a homologous recipient DNA molecule, and wherein the sequence of the donor DNA molecule is not identical with the sequence of the homologous recipient DNA molecule.

3. The method of claim 2, wherein the nucleotide sequence of the donor DNA molecule diverges from the nucleotide sequence of the homologous DNA molecule in the recipient cell by about 0.6% to about 5%.

4. The method of claim 2, wherein the nucleotide sequence of the donor DNA molecule diverges from the nucleotide sequence of the homologous DNA molecule in the recipient cell by about 0.6% to about 30% in the region where homologous recombination can take place.

5. The method of claim 2, wherein the mammalian recipient cell is obtained from a cell line that is cultured in vitro.

6. The method of claim 2, wherein the donor DNA molecule is a chromosomal DNA fragment that is inserted into a YAC or cosmid vector.

7. The method of claim 2, wherein the donor DNA molecule is a double-stranded oligonucleotide 10–100 bases in length, and wherein the nucleotide sequence of the donor DNA molecule diverges from the nucleotide sequence of the homologous DNA molecule in the recipient cell by at least one base pair, but no more than 5% of all base pairs.

8. The method of claim 2, wherein the donor DNA molecule is a single-stranded oligonucleotide 10–100 bases in length, and wherein the nucleotide sequence of the donor DNA molecule diverges from the nucleotide sequence of the homologous DNA molecule in the recipient cell by at least one base, but no more than 5% of all bases.

9. The method of claim 2, wherein the donor DNA molecule comprises a selectable marker gene flanked by two sequences, wherein one flanking sequence has at least 95% sequence identity to the corresponding sequence of the recipient DNA molecule and the other flanking sequence comprises a repetitive sequence.

10. The method of claim 9, wherein the repetitive sequence is a long interspersed element (LINE) or a short interspersed element (SINE).

11. A method of making a transgenic mouse, comprising (a) inserting a genetically modified stem cell prepared according to the method of claim 2 into a blastocoel, (b) implanting the blastocoel into a womb of a female host mouse to make the female mouse pregnant, and (c) carrying the pregnancy to term to obtain a viable transgenic mouse.

12. The method of claim 2, wherein at least one of the nucleotide base or base pairs in the donor DNA is modified in vitro prior to transformation.

13. The method of claim 12, wherein the modification is a point mutation, an insertion of base pairs, or a deletion of base pairs from the donor DNA molecule, and wherein the modified donor DNA molecule diverges from the nucleotide sequence of the homologous DNA molecule in the recipient cell by about 0.6% to about 5%.

14. The method of claim 12, wherein the modification is a point mutation, an insertion of base pairs, or a deletion of base pairs from the donor DNA molecule, and wherein the modified donor DNA molecule diverges from the nucleotide sequence of the homologous DNA molecule in the recipient cell by about 0.6% to about 30% in the region where homologous recombination can take place.

* * * * *

UNITED STATES PATENT AND TRADEMARK OFFICE
CERTIFICATE OF CORRECTION

| | |
|---|---|
| PATENT NO. | : 7,199,280 B2 |
| APPLICATION NO. | : 09/884877 |
| DATED | : April 3, 2007 |
| INVENTOR(S) | : Te Riele et al. |

It is certified that error appears in the above-identified patent and that said Letters Patent is hereby corrected as shown below:

Title page, right column, under Other Publications, "Promega Protocols and Appliccation Guide" should be --Promega Protocols and Application Guide--.

Col. 8, line 34, "muts" should be --mutS--.

Col. 8, line 59, after "dMsh2-9" insert --(ATCC deposit number RH532)--.

Col. 18, line 58, "Cheman" should be --Cherian--.

Col. 19, line 51, "Kinzier" should be --Kinzler--.

Col. 20, line 46, "Kinzier" should be --Kinzler--.

Col. 21, line 25, "lonov" should be --lonov--.

Col. 21, line 37, "Devi" should be --DevI--.

Col. 22, line 24, "Kinsier" should be --Kinzler--.

Signed and Sealed this

Fourteenth Day of August, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,199,280 B2 | Page 1 of 1 |
| APPLICATION NO. | : 09/884877 | |
| DATED | : April 3, 2007 | |
| INVENTOR(S) | : Te Riele et al. | |

It is certified that error appears in the above-identified patent and that said Letters Patent is hereby corrected as shown below:

Title page, right column, under Other Publications, "Promega Protocols and Appliccation Guide" should be --Promega Protocols and Application Guide--.

Col. 8, line 34, "muts" should be --mutS--.

Col. 8, line 59, after "dMsh2-9" insert --(ATCC deposit number RH532)--.

Col. 18, line 58, "Cheman" should be --Cherian--.

Col. 19, line 51, "Kinzier" should be --Kinzler--.

Col. 20, line 46, "Kinzier" should be --Kinzler--.

Col. 21, line 25, "lonov" should be --Ionov--.

Col. 21, line 37, "Devi" should be --DevI--.

Col. 22, line 24, "Kinzier" should be --Kinzler--.

This certificate supersedes the Certificate of Correction issued August 14, 2007.

Signed and Sealed this

Fourth Day of March, 2008

JON W. DUDAS
*Director of the United States Patent and Trademark Office*